US008016856B2

(12) United States Patent  (10) Patent No.: US 8,016,856 B2
Lavelle et al.  (45) Date of Patent: Sep. 13, 2011

(54) REMOVABLE HANDLE FOR MEDICAL DEVICE

(75) Inventors: Shay Lavelle, Annacotty (IE); Patrick Martin Kelly, Clarina (IE)

(73) Assignee: Cook Medical Technologies LLC, Bloomington, IN (US)

( * ) Notice: Subject to any disclaimer, the term of this patent is extended or adjusted under 35 U.S.C. 154(b) by 622 days.

(21) Appl. No.: 11/945,767

(22) Filed: Nov. 27, 2007

(65) Prior Publication Data

US 2008/0132940 A1  Jun. 5, 2008

Related U.S. Application Data

(60) Provisional application No. 60/872,344, filed on Nov. 30, 2006.

(51) Int. Cl.
*A61B 17/00* (2006.01)
(52) U.S. Cl. .................................................... 606/205
(58) Field of Classification Search .......... 606/205–209; D24/143; D8/52, 54; 29/255, 244, 270; 269/6; 16/110.1, 111.1, 113.1, 405, 406, 16/422, 426, 427, 429, 430, 431, 436
See application file for complete search history.

(56) References Cited

U.S. PATENT DOCUMENTS

| 2,113,246 A | 4/1938 | Wappler |
| 4,343,558 A | 8/1982 | Fujiwara |
| 4,721,116 A | 1/1988 | Schintgen et al. |
| 4,763,668 A | 8/1988 | Macek et al. |
| 4,815,476 A | 3/1989 | Clossick |
| 4,924,851 A | 5/1990 | Ognier et al. |
| 5,084,057 A | 1/1992 | Green et al. |
| 5,133,727 A | 7/1992 | Bales et al. |
| 5,213,113 A | 5/1993 | Hlinsky |
| 5,238,002 A | 8/1993 | Devlin et al. |
| 5,312,391 A | 5/1994 | Wilk |
| 5,391,166 A | 2/1995 | Eggers |
| 5,454,378 A * | 10/1995 | Palmer et al. ................. 600/564 |

(Continued)

FOREIGN PATENT DOCUMENTS

DE  94 09 979 U1  9/1994

(Continued)

OTHER PUBLICATIONS

EPO Search Report for EP Application No. 04 815 268.0, dated Jun. 13, 2007, 3 pages.

(Continued)

*Primary Examiner* — Gary Jackson
*Assistant Examiner* — Christopher Schubert
(74) *Attorney, Agent, or Firm* — Brinks Hofer Gilson & Lione

(57) ABSTRACT

A removable and replaceable handle for a medical device includes a main body with a distal end, a proximal end, and a longitudinal axis between the distal and proximal ends and a slider disposed within the main body that is translatable along the longitudinal axis between the distal and proximal ends. A first gripper is disposed within the slider and a second gripper is disposed within the main body, which are capable of retaining a control portion of the medical device when the slider is in the first position with a working portion of the medical device in a biased position, and allows the medical device to be removed from or inserted into the handle when the slider is in the second position.

18 Claims, 11 Drawing Sheets

U.S. PATENT DOCUMENTS

| | | |
|---|---|---|
| 5,456,683 A | 10/1995 | Fritzsch et al. |
| 5,569,284 A | 10/1996 | Young et al. |
| 5,630,818 A | 5/1997 | Del Rio et al. |
| 5,706,824 A | 1/1998 | Whittier |
| 5,785,647 A | 7/1998 | Tompkins et al. |
| 5,810,876 A | 9/1998 | Kelleher |
| 5,882,293 A | 3/1999 | Ouchi |
| 5,964,717 A | 10/1999 | Gottlieb et al. |
| 5,976,143 A | 11/1999 | McCue |
| 6,001,114 A | 12/1999 | Ouchi |
| 6,007,560 A | 12/1999 | Gottlieb et al. |
| 6,022,363 A | 2/2000 | Walker et al. |
| 6,033,424 A | 3/2000 | Ouchi |
| 6,059,719 A | 5/2000 | Yamamoto et al. |
| 6,080,180 A | 6/2000 | Yoon et al. |
| 6,142,956 A | 11/2000 | Kortenbach et al. |
| 6,197,001 B1 | 3/2001 | Wilson et al. |
| 6,206,904 B1 | 3/2001 | Ouchi |
| 6,283,924 B1 | 9/2001 | Ouchi |
| 6,378,351 B1 | 4/2002 | Ouchi et al. |
| 6,527,780 B1 | 3/2003 | Wallace et al. |
| 6,554,850 B1 | 4/2003 | Ouchi et al. |
| 6,575,977 B1 | 6/2003 | Michelson |
| 6,666,876 B2 | 12/2003 | Kawai et al. |
| 6,764,499 B2 | 7/2004 | Honey et al. |
| 7,169,167 B2 | 1/2007 | Chu |
| 7,316,703 B2 | 1/2008 | Suzuki |
| 2001/0034536 A1 | 10/2001 | Looper et al. |
| 2002/0165434 A1 | 11/2002 | Williamson, IV et al. |
| 2005/0137585 A1 | 6/2005 | Landman et al. |

FOREIGN PATENT DOCUMENTS

| | | |
|---|---|---|
| EP | 1 005 836 | 6/2000 |
| JP | 2005-323878 | 11/2005 |
| WO | WO 94/22377 | 10/1994 |
| WO | WO 02/41932 | 5/2002 |
| WO | WO 2005/063127 | 7/2005 |

OTHER PUBLICATIONS

International Search Report for International Application No. PCT/US2004/043168, dated Jun. 28, 2005, 3 pages.

International Search Report and Written Opinion for International Application No. PCT/US2007/085581, dated Apr. 21, 2008.

International Preliminary Report on Patentability for International Application No. PCT/US2007/085581, dated Jun. 11, 2009, 6-pages.

* cited by examiner

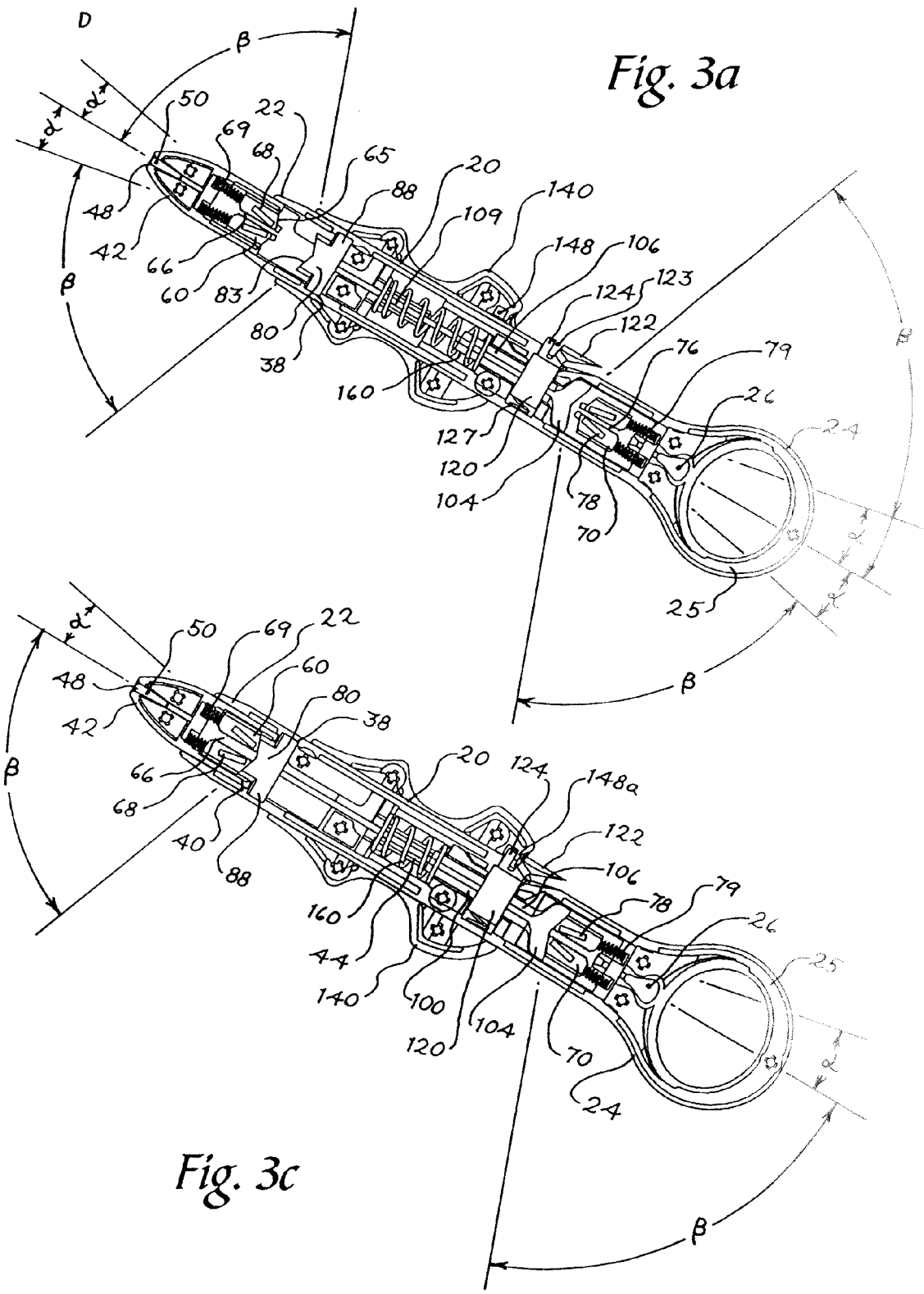

REMOVABLE HANDLE FOR MEDICAL DEVICE

CROSS-REFERENCE TO RELATED APPLICATIONS

This application claims priority from U.S. Provisional Application No. 60/872,344, filed on Nov. 30, 2006, the entirety of which is hereby fully incorporated by reference herein.

TECHNICAL FIELD

The field of the invention is that of medical and surgical instruments, and in particular, medical and surgical instruments intended primarily for minimally-invasive procedures. These instruments typically have a small diameter for entering body spaces or orifices of limited size.

BACKGROUND

One trend in modern surgery is the trend toward minimally-invasive procedures, in which laparoscopic or endoscopic procedures are used. These procedures tend to be less invasive to the patient, using a body orifice or a puncture into a body cavity or a natural existing space as an entry point for a medical device. Examples of entry points include a component of the urinary tract or the gastrointestinal system. These procedures are used in order to avoid major incisions for surgical access, accomplishing the medical procedure in less time with less risk to the patient, and with reduced patient convalescence.

Minimally invasive procedures thus provide benefits to the patient, in the sense that the procedures may be accomplished more quickly and more economically, and with less discomfort and less overall invasion of the body when compared to traditional open surgical techniques. Minimally-invasive procedures are not without their problems, however. One significant problem is that body orifices tend to be small, and thus minimally invasive surgical procedures may be difficult to accomplish due to the very small access provided. For example, when entering the urinary tract, space in the ureter is very limited, since this passage is only several millimeters in diameter. As a result, the majority of minimally invasive procedures are performed with an endoscope, particularly ureteroscopes in urinary tract cases. These ureteroscopes typically have a working channel that limits instruments or surgical tools to a diameter of about 3 Fr (1 mm).

Accordingly, remotely operable medical devices have been developed that have a working portion on a distal end of the device and a control portion on the proximal end of the medical device. The distal end portion can be threaded through the small working channel of endoscopes or similar instruments to allow for operation of the working portion with the proximal end portion of the medical device extending out of the patient through the endoscope. The working portions of the medical devices may be pivotable forceps jaws, movable graspers, baskets, cutters, snares or other types of tools that are selectively used to obtain a biopsy or tissue sample for a patient, or otherwise remotely perform a specific task when inserted into a patient. With reference to an example medical device shown in FIG. 11, the working portions of these medical devices may be substantially larger than the proximal end control portion of the medical device to allow for taking larger biopsies or tissue samples than would be possible if the working portion was substantially the same size as the proximal end portion of the device.

Because the jaws of the forceps may be significantly larger than the proximal end portion of the medical device, the proximal end portion of this type of medical device must be back loaded into an endoscope, or similar instrument. In other words, proximal end portion of the medical device is inserted into the front end of the endoscopic instrument prior to the instrument being manipulated within the patient. A representative example of a back loading endoscopic instrument suitable for use with the handle disclosed in this specification was disclosed in U.S. Ser. No. 11/020,328 filed on Dec. 22, 2004, titled "Back Loading Endoscopic Instruments," and is assigned to a related subsidiary of the assignee of this application, and is fully incorporated by reference herein in its entirety.

In operation, with reference to an exemplary forceps medical device shown in FIG. 11, when a proximal end 804 of a medical device 800 is inserted into an endoscope, or similar instrument, the proximal end 804 of the medical 800 normally extends out of the proximal, or rear end, of the endoscope to allow for operation of the forceps biopsy cups, or jaws 810 by the physician. Typically, the control, or proximal end, portion of the forceps medical device 800 includes a central wire 820 and an outer sheath 830, both of which are operatively connected to a pair of biopsy cups 810 that pivot within a housing 814. Central wire 820 and outer sheath 830 are joined together at the proximal end portion 804 of the forceps medical device 800. When the outer sheath 830 and the central wire 820 are in a relaxed state, the forceps jaws 810 are biased away from each other in a relaxed position. When the outer sheath 830 is placed in tension, or stretched, with respect to the central wire 820, the biopsy cups 810 rotate toward each other (in a biased position) against the biasing force of the housing 814 to obtain a tissue sample, or biopsy from the patient. When tension in the outer sheath 830 is released, the biopsy cups 810 extend away from each other due to the biasing force of arms that extend from the biopsy cups 810 and return to the relaxed position.

Often during medical procedures, medical devices that are used with an endoscope are inserted into the appropriate location within the patient through an access sheath. Additionally, to minimize the amount of discomfort and damage done by the working or operable portion of the medical device as it is advanced to the desired location, it is preferred to insert the device within the patient with the working portion in a closed, or biased, position, rather than an open, or relaxed, position. With continued reference to FIG. 11 and as discussed above, biopsy cups 810 are transferred to the closed position (i.e. the biopsy cups 810 rotate toward opposite jaws 810 until they contact each other) when the outer sheath 830 is held in tension with respect to the central wire 820.

To maintain the biopsy cups 810 in the closed position, the physician or another medical professional must manually maintain the stretch in the outer sheath 830 as the working portion of the medical device is advanced to the desired location within the patient. Because it often takes a significant period of time to properly position the medical device in the patient, it is often a labor intensive and tiresome procedure to maintain the outer sheath 830 in tension to ensure that the biopsy cups 810 remain in the closed position during the insertion and also during operation and removal. Accordingly, it is desired to obtain a mechanism that can maintain the operable portion of a medical device in a closed position without requiring a medical professional to manually maintain the outer sheath stretched during insertion, placement, operation, and removal of the medical device 800 and the endoscopic instrument within the patient.

BRIEF SUMMARY

The first aspect of the present invention provides a handle for retaining and operating a medical device. The handle includes a main body with a distal end, a proximal end, and a central axis between the distal and proximal ends. A slider is provided that is movably disposed along the longitudinal axis of the main body between a first position and a second position. A first pair of grippers is slidably engaged within the slider and a second pair of grippers is slidably engaged within the main body. Each of the first and second sets of grippers are biased toward their opposite respective gripper when the slider is in the first position and each of the respective first and second sets of grippers translate away from each opposite respective gripper as the slider translates toward the second position.

A second aspect of the present invention provides a handle for remotely operating a medical device with a working portion and a control portion. The handle includes a main body with a distal end, a proximal end, and a longitudinal axis between the distal and proximal ends. A slider is provided that is movable within the main body along the longitudinal axis. A first gripper is operatively connected to the slider and a second gripper is operatively connected to the slider and disposed proximally of the first gripper. Longitudinal movement of the slider with respect to the main body causes the first and second grippers to change position.

A third aspect of the present invention provides a handle for remotely operating a medical device that includes a working portion and a control portion separated from the working portion. The handle includes a main body with a distal end, an opposite proximal end, and a longitudinal axis. A slider is disposed within the main body to translate between a first position and a second position with respect to the main body. A first pair of grippers are disposed within the slider and a second pair of grippers disposed within the main body, wherein the first and second pairs of grippers selectively retain the control portion of the medical device when the slider is in the first position and the control portion of the medical device can be inserted or withdrawn from the first and second pairs of grippers when the slider is in the second position. Further, the working portion of the medical device is in a biased position when the slider is in the first position and the working portion of the medical device is in a relaxed position when the slider is in the second position.

A fourth aspect of the present invention provides a handle for remotely operating a medical device that includes a main body comprising a distal end, a proximal end, and a longitudinal axis between the distal and proximal ends. A slider is movable within the main body along the longitudinal axis. A first means for gripping the control portion of the medical device is operatively connected with the slider and a second means for gripping the control portion of the medical device is operatively connected with the slider and proximal of the first means for gripping.

Advantages of the present invention will become more apparent to those skilled in the art from the following description of the preferred embodiments of the invention that have been shown and described by way of illustration. For example, the handle may be used to remotely operation a plurality of types of medical devices that include a control portion with a sheath and a coaxial inner wire on a proximal or control portion of the medical device. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 3a is the view of the handle of FIG. 1 with a portion of the main body, the slider, and the spool removed showing the handle in a first position.

FIG. 3c is the view of the handle of FIG. 3a showing the handle in a second position.

FIG. 10b is a bottom perspective view of the gripper of FIG. 10a.

FIG. 10c is an opposite perspective view of the gripper of FIG. 10a.

DETAILED DESCRIPTION OF THE DRAWINGS AND THE PREFERRED EMBODIMENTS

Figure 1:
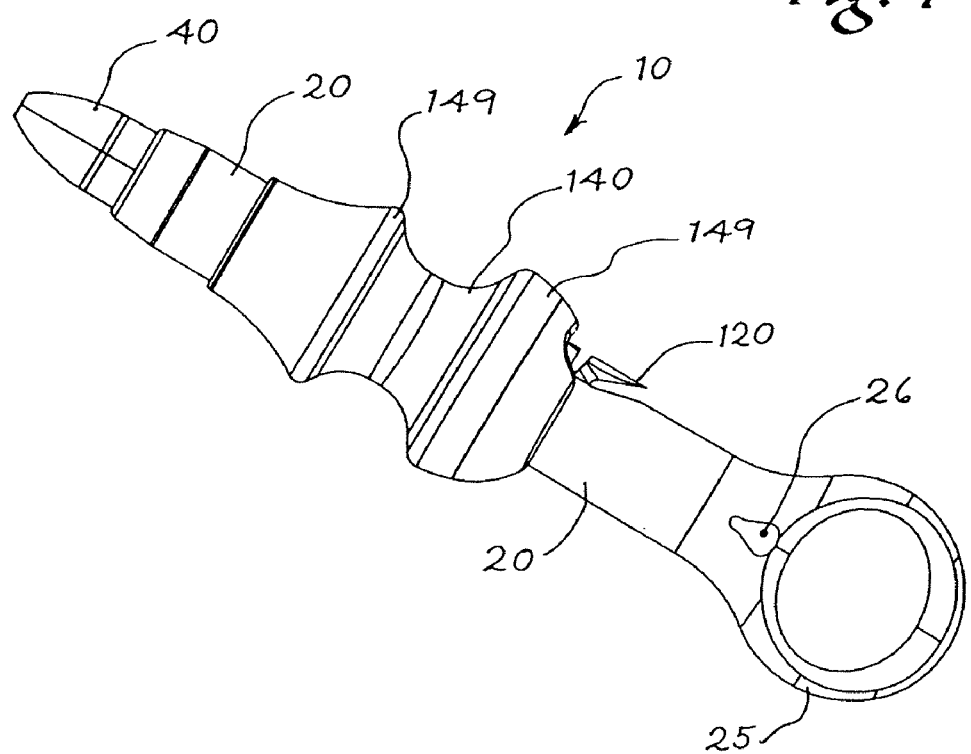
FIG. 1 is a side view of a handle for a medical device.
Figure 2:
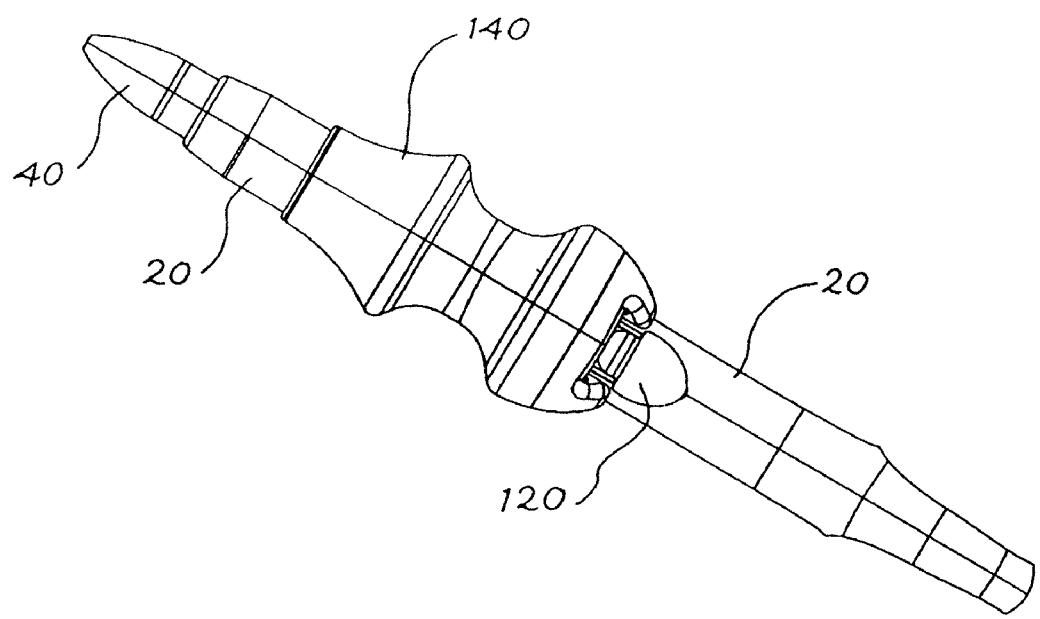
FIG. 2 is a top view of the handle of FIG. 1.

Turning now to the embodiments shown in FIGS. 1-10, a handle 10 for an endoscopic medical device is provided. The handle 10 includes a main body 20, a slider 40 that is mounted within the main body 20 to translate or slide along a longitudinal axis 36 of main body 20 between a first position (best shown in FIG. 3a) wherein a medical device is held by the handle 10 with the working portion of the medical device in a biased position, to a second position (best shown in FIG. 3c) when the medical device may be removed from or inserted into handle 10 and the working portion of the medical device is in a relaxed position. Slider 40 is rigidly connected with a spool 140 that surrounds main body 20 and provides a surface for the user to manipulate to translate slider 40 within main body 20 between the first and second positions.

A set of front grippers 60 and a set of rear grippers 70 are provided within handle 10. Front grippers 60 include two gripping members that are enclosed within slider 40 and disposed between slider 40 and a front gripper guide 80 that is rigidly connected to main body 20. Rear grippers 70 include two gripping members that are enclosed within main body 20 and are disposed between main body 20 and a rear gripper guide 100 that translates with the movement of slider 40. As slider 40 translates between the first position and the second position, each of the front and rear grippers 60, 70 selectively move away from the opposite member of front and rear grippers 60, 70. A button 120 is translatably mounted within main body 20 to selectively retain spool 140 and slider 40 in the second position and to limit the travel of spool 140 and slider 40 toward the second position when button 120 is not compressed.

Figure 4:
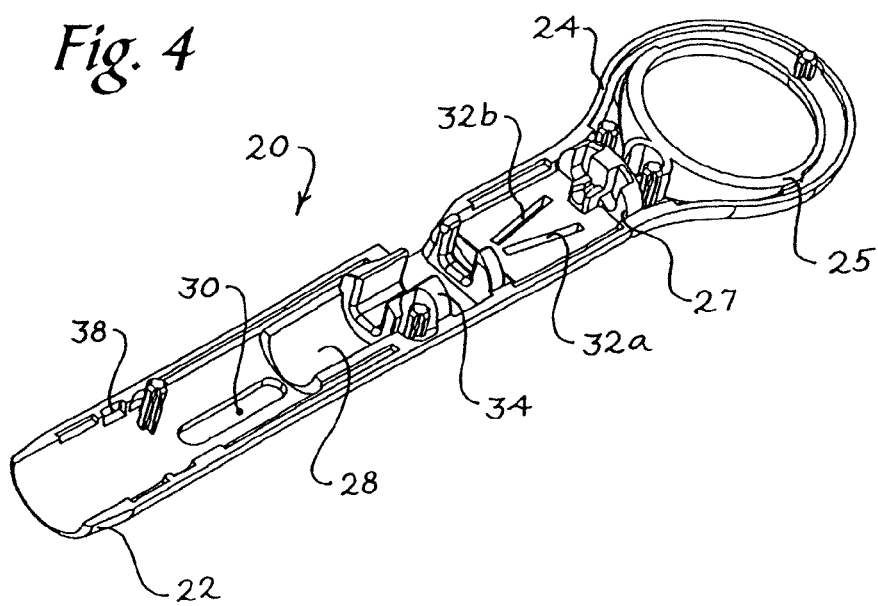
FIG. 4 is an exploded view of the main body of the handle of FIG. 1 with half of the main body rotated to view the internal structure of that half.
Figure 4B:
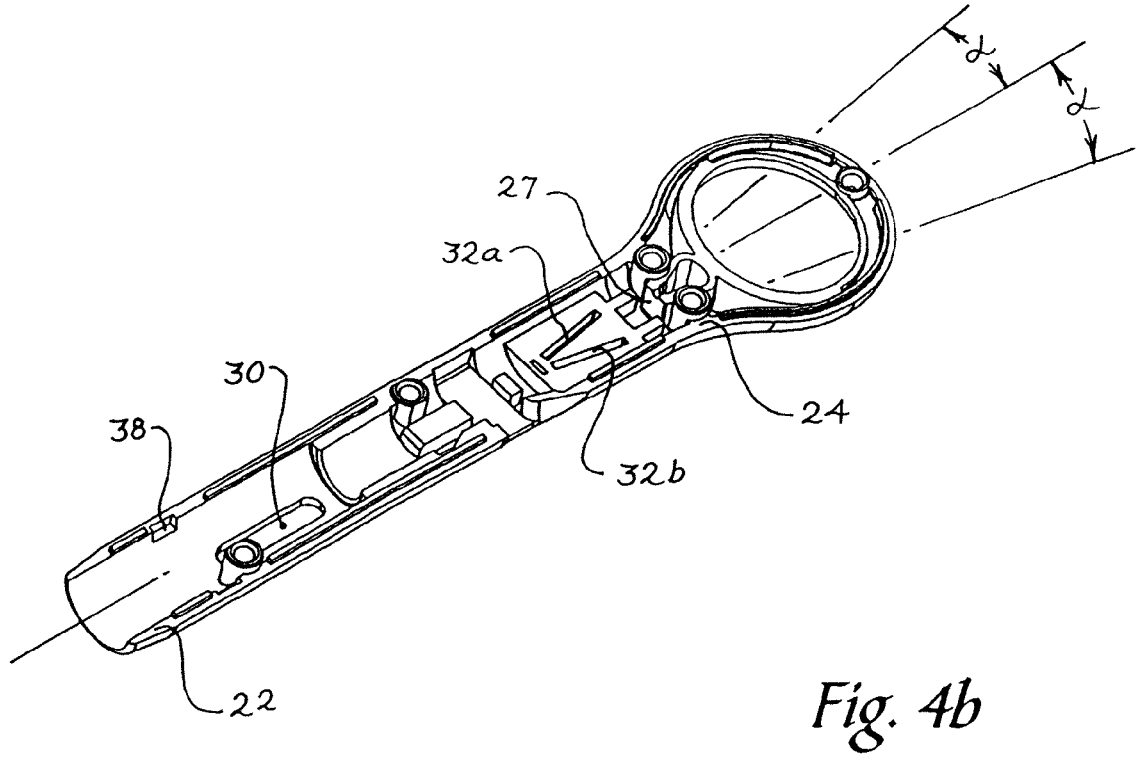

As best shown in FIG. 4, main body 20 includes a distal end 22, a proximal end 24, and a longitudinal axis 36 that extends between distal and proximal ends 22, 24. Main body 20 may be molded from two clamshell halves that are press fit together during assembly or joined by other means such as adhesive, ultrasonic welding, snap fit, etc. Main body 20 is substantially hollow from open distal end 22 to the proximity of proximal end 24. Proximal end 24 may include a ring 25 that is suitable to receive the user's thumb to allow handle 10 to be operated by a single hand.

As shown in FIGS. 3a-3c and 4, main body 20 includes two opposite locator recesses 38 in the vicinity of distal end 22 of main body to receive each of the two side arms 88 of front gripper guide 80 to maintain a rigid connection between main body 20 and front gripper guide 80. Main body 20 includes at least one slider channel 30, preferably two slider channels 30 defined on each opposite clam shell half of main body 20. Slider channel 30 receives at least one peg 146 that extends from a distal end 142 of spool 140 and is connected with a corresponding hole 48 on slider. The length of slider channel 30 may define the length of possible travel of slider 40 with respect to main body 20. In other embodiments, the length of travel of the slider 40 with respect to the main body may be defined by an upstanding surface 53 within slider 40 that contacts the front gripper guide 80 (discussed below) when handle 10 is in the first position shown in FIG. 3a.

Main body 20 further includes a cavity 28 to receive a main spring 160 formed proximally of slider channel 30. As discussed below, and shown in FIGS. 3a-3c, main spring 160 is biased between a proximal end 44 of slider 40 and a forward face of main body 20 that defines a sliding core channel 34. Main spring 160 biases slider 40 in the direction of distal end 22 of main body (i.e. toward the first position shown in FIG. 3a), which retains first and second sets of grippers 60, 70 engaged with their respective opposite gripper members or retains the control portion of a medical device in tension to maintain the forceps jaws closed when a proximal end of a medical device is inserted into handle 10.

Each clam shell half of main body 20 includes two grooves 32a, 32b defined within main body 20. Grooves 32a, 32b are each normally aligned at the same (and opposite) oblique angles α with respect to longitudinal axis 36 of main body. In some embodiments, angle α may between about 1 degree and about 45 degrees from longitudinal axis 36. Preferably, angle α is between about 5 degrees and about 15 degrees. More preferably, angle α is about 10 degrees for longitudinal axis 36.

Figure 10A:
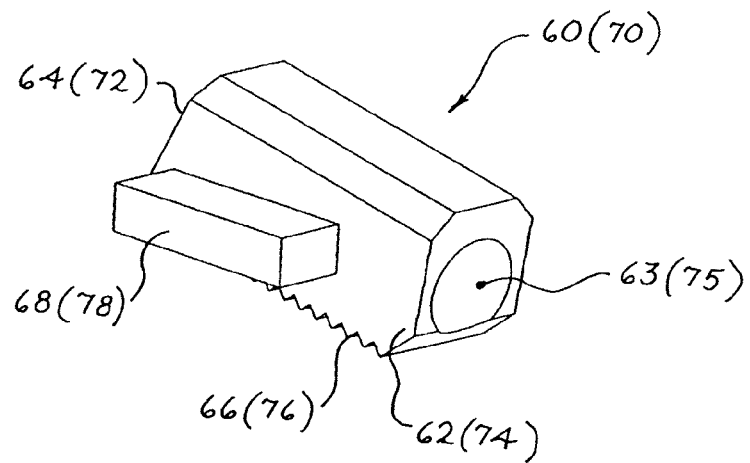
FIG. 10a is a perspective view of a gripper of the handle of FIG. 1.
Figure 10B:
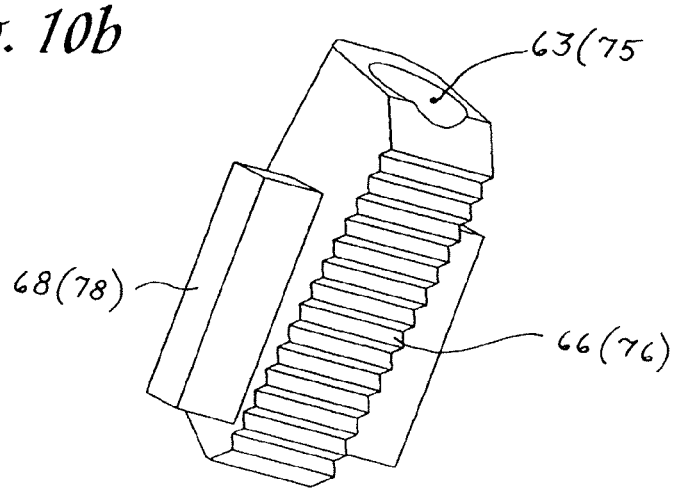
Figure 10C:
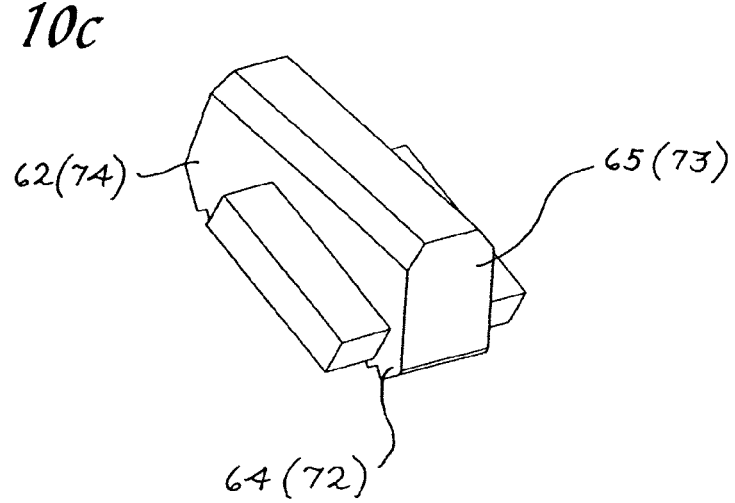

Grooves 32a, 32b receive projections 78 that extend from each of the rear grippers 70 and define the range of travel of rear grippers 70 with respect to main body 60. With reference to FIGS. 10a-10c, projections 78 are aligned at the same angle α with respect to the toothed surface 76 of the rear grippers 70 as the grooves 32a, 32b are aligned with respect to the longitudinal axis 36 of the main body 20.

As projections 78 from rear grippers 70 move toward proximal end 24 of main body 20 along grooves 32a, 32b, rear grippers 70 translate away from each other until teeth 76 of grippers 70 no longer engage each other or the proximal end portion of the inserted medical device, which allows the proximal end portion of the medical device to be withdrawn from or inserted into the handle 10. Conversely, as projections 78 from rear grippers 70 slide toward distal end 22 of main body 20 within grooves 32a, 32b, rear grippers 70 translate toward each other until teeth 76 engage each other, or engage the proximal end portion of the medical device and retain the medical device within handle 10. As discussed below, the engagement between the rear grippers 70 and the proximal end portion of the medical device aids in establishing the tension in the outer sheath of the proximal end portion to manipulate the operable portion of the medical device.

In addition to thumb ring 25, proximal end 24 of main body 20 may include a viewing window 26 that receives the proximal end portion of the medical device and gives the user an indication that the proximal end, or control portion, of the medical device is fully inserted into handle 10. Further, proximal end 24 includes a biasing surface 27 that is contacted by a set of rear springs 79 provided between main body 20 and rear grippers 70 to bias rear grippers 70 toward rear gripper guide 100.

Figure 5:
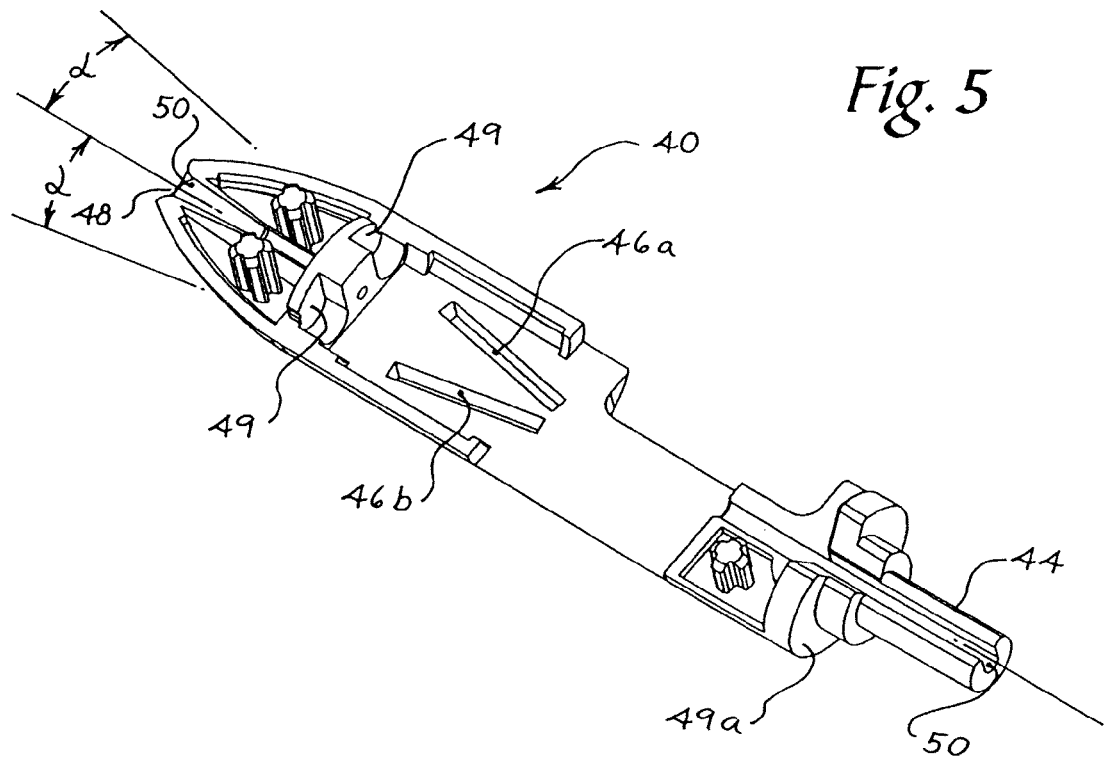
FIG. 5 is an exploded view of the slider of the handle of FIG. 1.
Figure 5B:
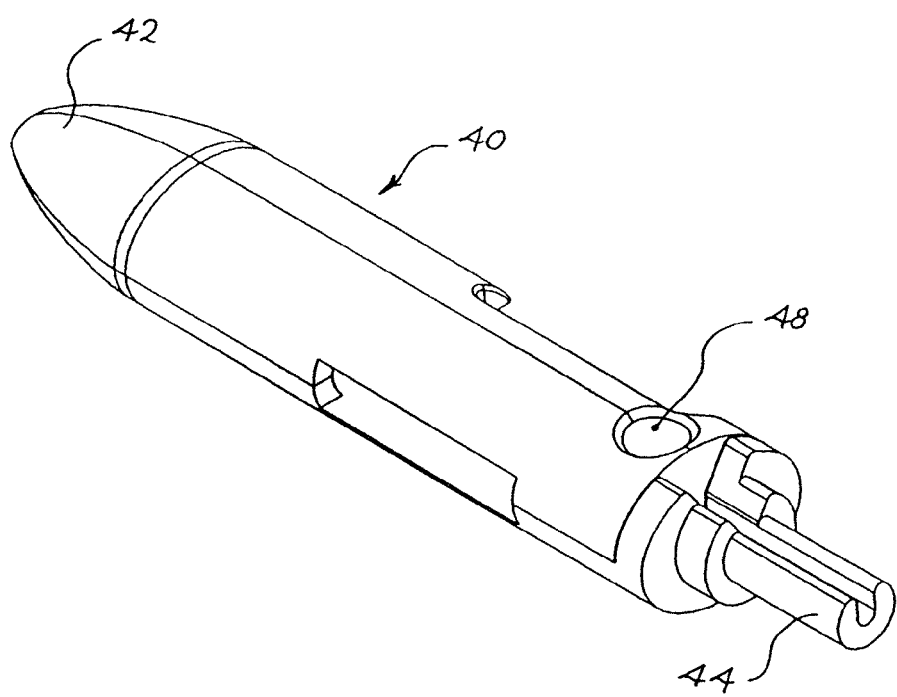

Turning now to FIG. 5, slider 40 may be formed from two molded clam shell halves that may be press fit together during assembly, or joined with other means such as an adhesive, ultrasonic welding, snap fit, etc. Slider 40 includes a central aperture 50 that extends through the entire length of slider 40 to receive the proximal end portion of the medical device. Further, a cannula 109 may be provided within slider 40 to further assist threading the medical device through slider 40. Slider 40 includes a biasing surface 49 that is contacted by a set of forward springs 69 that are provided between slider 40 and the pair of front grippers 60 to bias front grippers 60 toward front gripper guide 80. Slider additionally includes two grooves 46a, 46b defined proximally of biasing surface 49 and formed at oblique angles α with respect to longitudinal axis 36 of main body 20. Angle α maybe between about 1 degree and about 45 degrees with respect to the longitudinal axis 36 of main body. Preferably, the angle α may be between about 5 degrees and about 15 degrees with respect to longitudinal axis 36 of main body. More preferably angle α may be about 10 degrees with respect to longitudinal axis 36 of main body.

Grooves 46a, 46b receive projections 68 from each of the front set of grippers 60 and define the range of travel of front grippers 60 with respect to slider 40. With reference to FIGS. 10a-10c, projections 68 are aligned at the same angle α with respect to the toothed surface 66 of the front grippers 60 as the grooves 46a, 46b are aligned with respect to longitudinal axis 36 of main body 20.

Figure 3B:
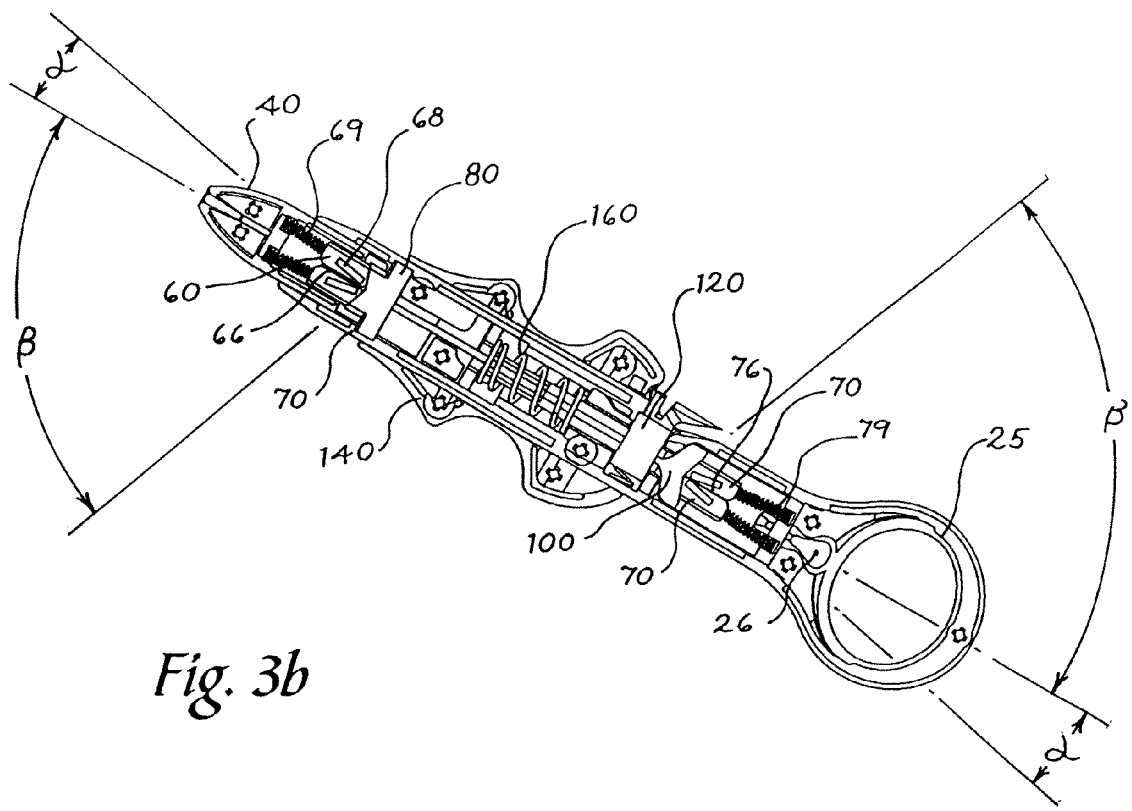
FIG. 3b is the view of the handle of FIG. 3a showing the handle in an intermediate position.

As slider 40 is translated from the first position (FIG. 3a) toward the second position (FIG. 3c) in the direction of proximal end 24 of main body 20, front grippers 60 are moved closer to distal end 42 of slider 40 because front gripper guide 80 is fixed to main body 20 with side arms 88 of front gripper guide 80 received within locator recesses 38 on main body 20. As front grippers 60 translate along grooves 46a, 46b, front grippers 60 translate away from each other due to the orientation grooves 46a, 46b at oblique angle α with respect to longitudinal axis 36 of main body 20. As opposing front grippers 60 translate away from each other, teeth 66 from opposing front grippers 60 no longer engage each other or the proximal end portion of the medical device at some point between the first and intermediate positions (FIGS. 3a, 3b). Eventually, opposite teeth 66 of front grippers 60 no longer contact the proximal end portion of the medical device to release the tension on the outer sheath, which allows the working portion of the medical device to translate to the relaxed position.

As slider 40 returns toward the first position, front springs 69 move front grippers 60 in the direction of proximal end 24 of main body 20, causing front grippers 60 to translate toward each other due to the oblique angle α of grooves 46a, 46b until teeth 66 contact the outer sheath of the proximal end of the medical device (if inserted into cavity 50 of slider 40), or the teeth 66 of the opposing front gripper 60. As slider 40 further translates toward the first position, the engagement between front and rear grippers 60, 70 and the relative motion between the two sets of grippers away from each other causes the outer sheath to stretch, and the working portion of the medical device translates to the biased position.

Figure 12:
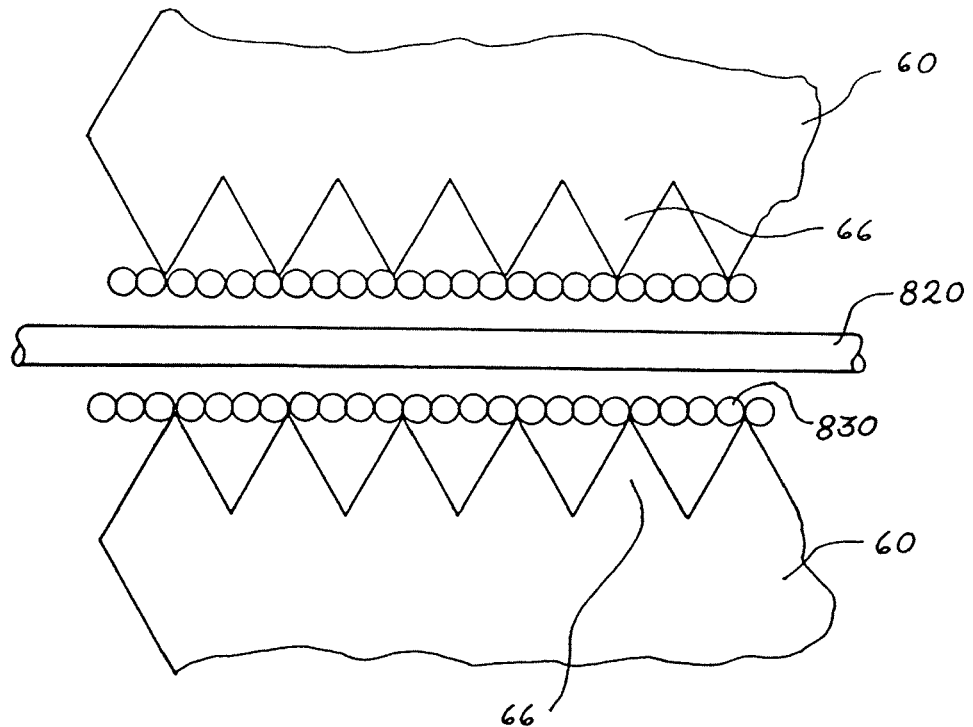
FIG. 12 is a schematic view of the teeth of the gripper of FIG. 10a engaging the endoscopic forceps of FIG. 11.
Figure 1B:
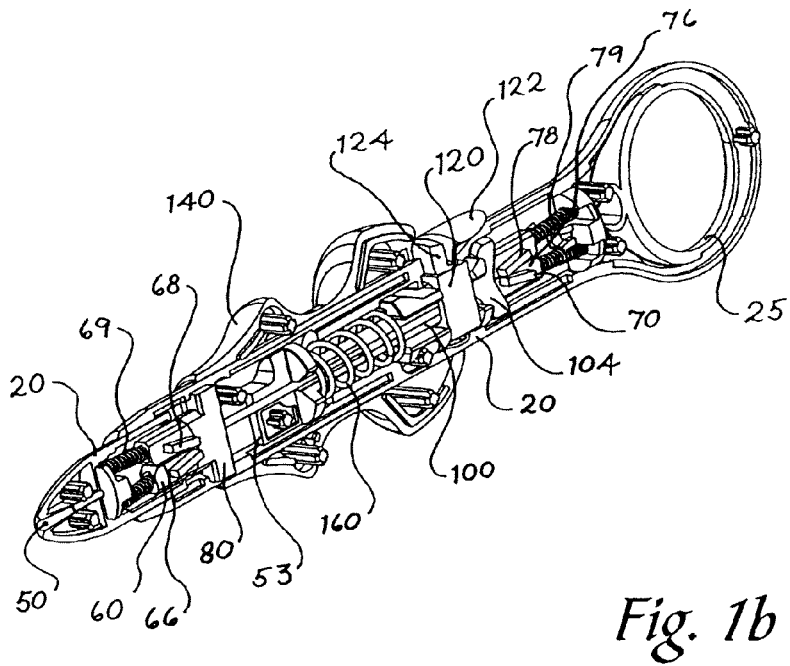
FIG. 1b is a front perspective view of the handle of FIG. 1 with a portion of the spool, main body, and slider removed.
Figure 11:
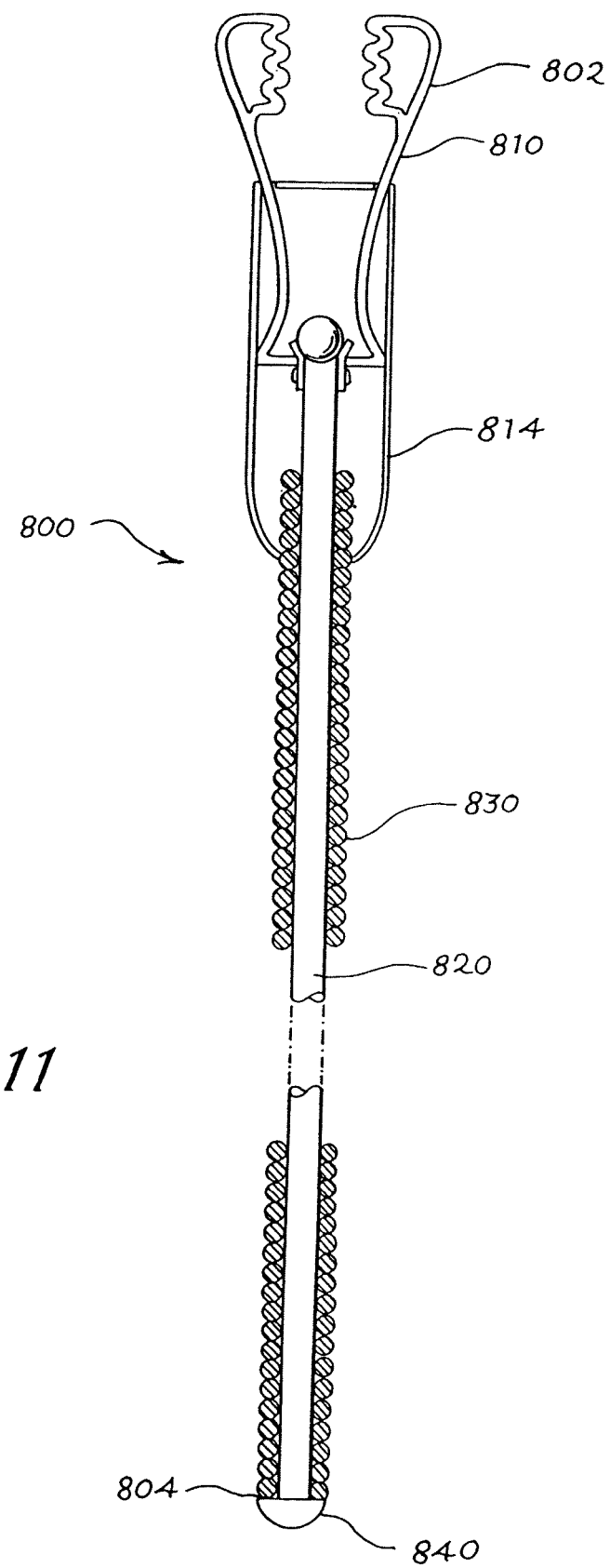
FIG. 11 is a side view of a prior art set of back loading endoscopic forceps.

While springs 69, 79 are provided to correctly position front and rear grippers 60, 70, the springs 69, 79 do not provide the majority of the clamping force used to retain the tension in the outer sheath of the proximal end portion of the medical device. Instead, front and rear opposing grippers 60, 70 become wedged against each other as they slide toward each other (and contact the proximal end of the medical device if inserted into the handle). The wedging connection of opposing members of front and rear grippers 60, 70 causes opposing compressive forces on the outer sheath of the medical device, which prevents the medical device from sliding with respect to front and rear grippers 60, 70 when slider 40 is in the first position. In some embodiments used with medical devices similar to that shown in FIG. 11 with a coiled wire outer sheath, as shown in FIG. 12 neighboring teeth 66, 76 of the respective first and second grippers 60, 70 are spaced apart from neighboring teeth a distance approximately equal to a whole number of diameters of the coiled wire forming the outer sheath. Specifically, the neighboring teeth 66, 76 may be spaced apart a distance equal to 1, 2, 3, 4, 5, 6, or any other number of diameters of the coiled wire.

Further, grooves 32a, 32b on main body 20 and grooves 46a, 46b are each disposed at oblique angle α with respect to longitudinal axis 36 of main body 20. Grooves 32a, 32b and grooves 46a, 46b each extend obliquely upward from longitudinal axis 36 of main body 20 in opposing directions. In operation with the proximal end portion of the medical device inserted within handle 10, each of front and rear grippers 60, 70 stretch the outer sheath of the medical device as slider 40 translates toward the first position, which translates the working portion of the medical device to a biased position. For example, when the medical device is a set of forceps, the biopsy cups of the forceps device pivot to engage each other.

As discussed above, holes 48 are provided at proximal end 44 of each clamshell portion of slider 40 to receive pins 146 that extend from spool 140 and are inserted through slider channels 30 in main body 20. In some embodiments, the connection between pins 146 of spool 140 and slider channel 30 in main body 20 defines the potential range of movement of slider 40 with respect to main body 20. In other embodiments, the length of travel of the slider 40 with respect to the main body may be defined by an upstanding surface 53 within slider 40 that contacts the front gripper guide 80 (discussed below) when handle 10 is in the first position shown in FIG. 3a. Proximal end 44 of slider 40 provides the forward biasing surface 49a for main spring 160, which urges slider 40 toward the first position. When slider 40 is in the first position, front and rear grippers 60, 70 engage toward their opposite grippers teeth 60, 70, to place tension on the outer sheath of the medical device.

Figure 6:
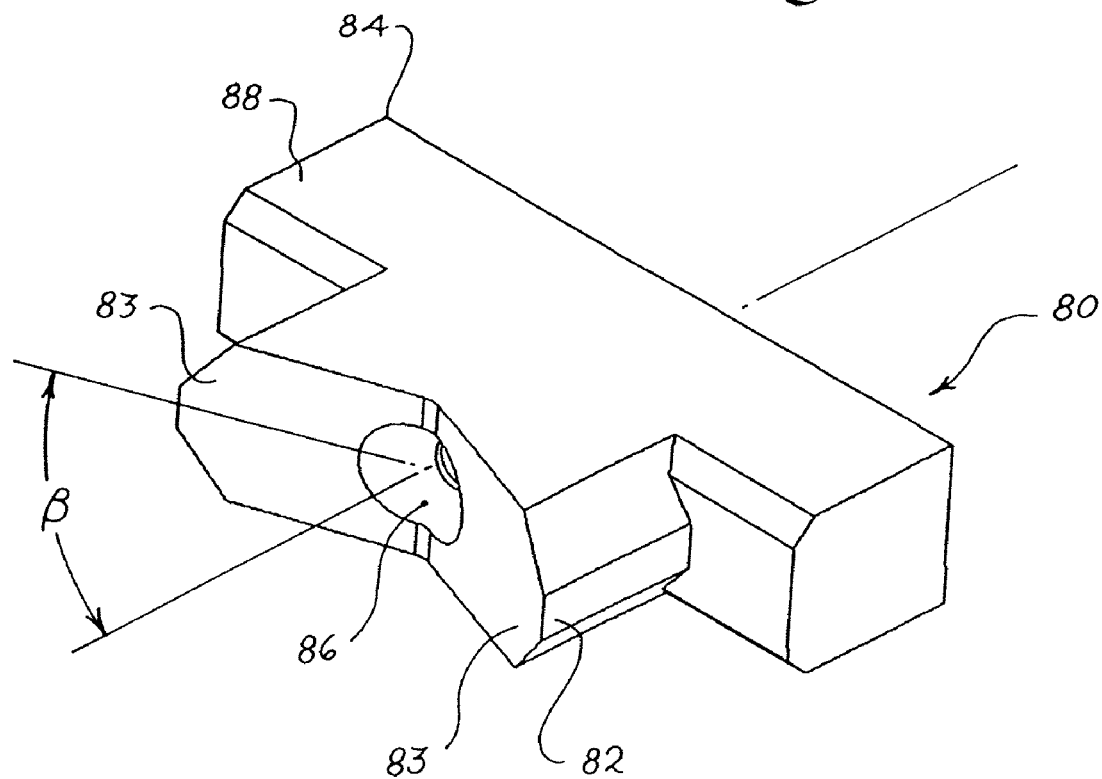
FIG. 6 is a perspective view of the front gripper guide of the handle of FIG. 1.

Turning now to FIG. 6 with continued reference to FIGS. 3a-3c, a front gripper guide 80 is provided. Front gripper guide 80 includes two oppositely extending side arms 88 that are received within locators 38 defined in main body 20 to fix front gripper guide 80 with respect to main body 20. Front gripper guide 80 includes a through hole 86 to provide clearance for the proximal end portion of the medical device to be inserted through front gripper guide 80 and the remainder of handle 10. Cannula 109 may be inserted through a portion of hole 86 through the rear end of front gripper guide 80. Front gripper guide 80 is enclosed within slider 40, while allowing for relative movement between slider 40 and front gripper guide 80 due to the fixed connection between main body 20 and front gripper guide 80.

Front gripper guide 80 also includes a distal end 82 with two opposing front faces 83 that are aligned at oblique angles β to the longitudinal axis 80a of front gripper guide 80. Angle β may be any angle between about 45 degrees and about 89 degrees with respect to longitudinal axis 36 of main body. Preferably, angle β may be between about 60 degrees and about 80 degrees. More preferably, angle β may be about 70 degrees. In some embodiments, angle β may be a complimentary angle to angle α between longitudinal axis 36 of main body 20 and grooves 46a, 46b.

As understood with reference to FIGS. 3a-3c, as slider 40 is translated with respect to main body 20 (due to the user manipulating spool 140), front grippers 60 are urged toward distal end 42 of slider 40 with the aid of grooves 46a, 46b. As front grippers 60 are urged toward distal end 42 of slider 40, front springs 69 are compressed and rear faces 65 of front grippers 60 slide obliquely upward along front faces 83 of front gripper guide 80. When spool 140 is released by the user, slider 40 translates distally along main body 20 toward the first position due to the biasing force of main spring 160. Accordingly, front springs 69 decompress, which allows front grippers 60 to translate proximally with respect to slider 40 along grooves 46a, 46b.

Front and rear grippers 60, 70 are best shown in FIGS. 10a-10c and may be formed with identical geometry. As discussed above, both front and rear grippers 60, 70 include projections 68, 78 that extend from both side surfaces of the grippers 60, 70, which extend into corresponding grooves 32a, 32b of main body 20 or grooves 46a, 46b of slider 40. Further, grippers 60, 70 include a plurality of teeth 66, 76 that engage the outer sheath of the proximal end portion of the medial device. When the medical device is not inserted into handle 10, opposing front and rear grippers 60, 70 are free to engage their opposing pair of front and rear grippers 60, 70. Projections 68, 78 are oriented at the same angle α with respect to a plane that extends through the apexes of the teeth 66, 76 of the front and rear grippers 60, 70, respectively. In some embodiments, front grippers 60 do not contact front gripper guide 80 when slider 40 is in the first position and front grippers 60 translates toward contact with front gripper guide 80 as slider 40 is translated toward the second position.

Further, grooves 32a, 32b on main body 20 and grooves 46a, 46b are each disposed at angle α with respect to longitudinal axis 36 of main body 20 in opposing directions. Accordingly, front and rear grippers 60, 70 pull the outer sheath of medical device in opposite directions when the slider 40 moves toward the first position.

As disclosed in co-pending U.S. Ser. No. 11/020,328, filed on Dec. 22, 2004 titled "Back Loading Endoscopic Instruments" and assigned to a subsidiary of the assignee of the subject application, a medical device with a working end and a proximal end control portion may be constructed with an outer sheath on the proximal end portion that may be formed from a coil of thin metal wire. The outer sheath surrounds and is joined to both a proximal end of an internal wire of the medical device and the housing that mechanically engages the working portion of the medical device.

As shown in FIG. 12, the tips or points of each of tooth 66, 76 of each gripper 60, 70 are preferably spaced apart a distance that is a multiple number of diameters of the wire that forms the coiled outer sheath so that the teeth 66, 76 of front and rear grippers 60, 70 engage the space between neighboring coils of wire. In some embodiments, neighboring teeth 66, 76 are spaced apart a distance equivalent to any of 1-6 diameters of the wire forming the coiled outer sheath. In other embodiments, the neighboring teeth 66, 76 may be spaced at different lengths from each other. Alternatively, neighboring teeth 66, 76 may be spaced apart different lengths from neighboring teeth 66, 76 within the same gripper. For example, a first pair of neighboring teeth may be spaced apart a distance equal to three diameters of the coiled wire outer sheath, and another pair of neighboring teeth on the same gripper may be spaced apart a distance equal to 4 diameters of the coiled wire outer sheath. This arrangement provides for a strong grip between teeth 66, 76 and the coiled outer sheath and prevents the outer sheath from easily sliding along teeth 66, 76 of front and rear grippers 60, 70 when slider 40 travels toward the first position.

Figure 7:
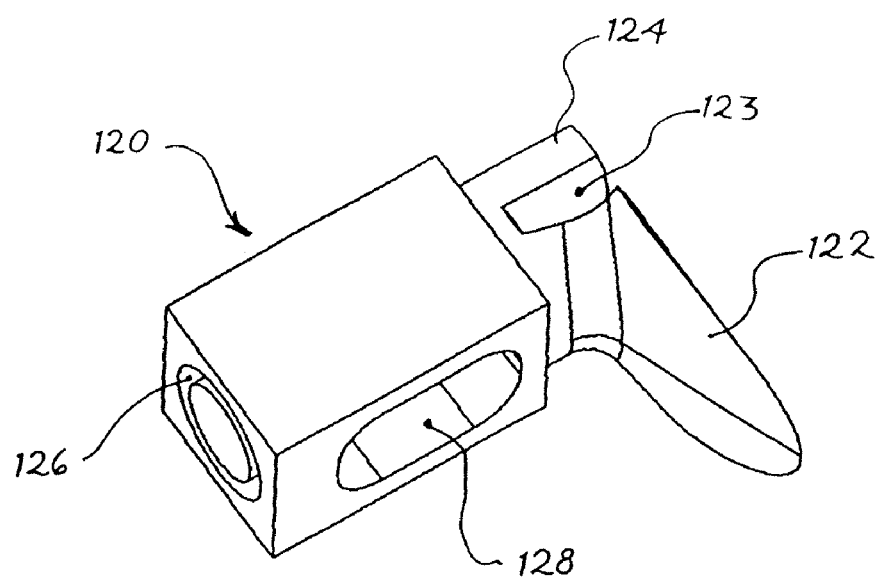
FIG. 7 is a perspective view of the button of the handle of FIG. 1.

Turning now to FIG. 7 with continued reference to FIGS. 3a-3c, button 120 is translatably mounted within main body 20. Button 120 includes an operable portion 122 and a protruding portion 124 that each are formed on a top surface of button 120 that extends out of main body 20. A recess 123 is defined between operable portion 122 and protruding portion 124 that receives a shelf 148a of cutout 148 of spool 140 (discussed below) to retain spool 140 and slider 40 in the second position. Button 120 additionally includes an aperture 128 that extends through button 120 to receive a sliding core 106 of rear gripper guide 100, discussed below. Aperture 128 is formed with a similar non-circular cross-section to the sliding core 106 to prevent relative rotation between button 120 and rear gripper guide 100. Aperture 128 is formed with a height equivalent to the sliding core 106 in addition to the length of potential linear travel of button 120. Button 120 is biased upward (i.e. in the direction where operable and protruding portions 122, 124 of button 120 extend out of main body 20) by a button spring 127 (FIG. 3c) disposed between button 120 and main body 20.

As discussed above, protruding portion 124 of button 120 is engageable with spool 140 when slider 40 is transferred to the second position. As can be best understood with reference to FIGS. 3a-3c, button 120 must be depressed against the biasing force of button spring 127 to temporarily translate protruding portion 124 below proximal end 144 of spool 140 to provide clearance for spool 140 and slider 40 to reach the second position. If spool 140 is pulled rearward without compressing operable portion 122 of button 120, proximal end 144 of spool 140 contacts the front of protruding portion 124 of button to prevent further rearward movement of slider 40 past the intermediate position shown in FIG. 3b.

As slider 40 translates toward the intermediate position, front and rear grippers 60, 70 feel compressive forces due to the increased biasing force of their respective springs 69, 79 due to the movement of slider 40 with respect to main body 20. As the compression of springs 69, 79 increases, grippers 60, 70 translate on the ramp faces 83, 105 of the respective front and rear gripper guides 80, 100 away from the longitudinal axis 36 of the main body 20. In some embodiments, where spool 140 engages protruding portion 124 of button 120, rear grippers 70 are still engaged with the proximal end portion of the medical device, which allows handle 10 to maintain its hold on the medical device.

In some embodiments, front grippers 60 release the medical device just prior to spool 140 contacting button 120 as spool 140 translates between the first and intermediate positions. This removes the stretch in the outer sheath of the medical device (allowing the working portion to translate to the relaxed state) while rear grippers 70 continue to engage the medical device to retain the medical device within handle 10. Rear grippers 70 release the medical device just after spool 140 is translated past the intermediate position on the way to the second position.

Figure 8:
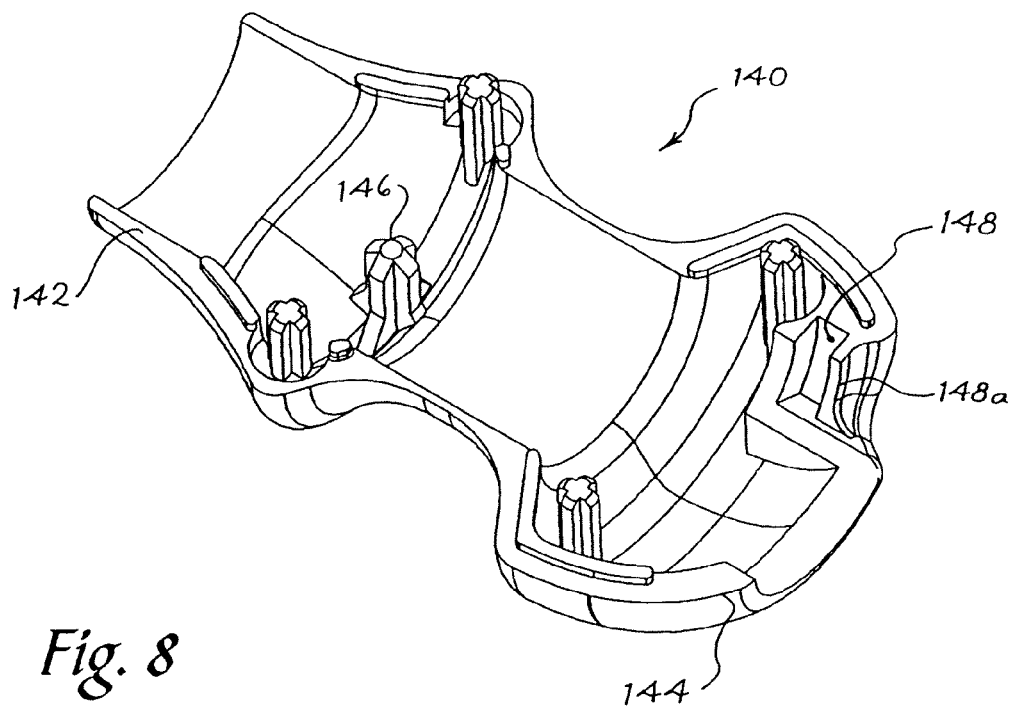
FIG. 8 is a perspective view of the internal surface of a portion of the spool of the handle of FIG. 1.

Spool 140 is best shown in FIGS. 1 and 8. Spool 140 may be formed from two clamshell halves that are press fit or attached together in other ways such as with adhesive, ultrasonic weld, snap fit or otherwise attached during assembly of handle 10. As discussed above, spool 140 includes distal end 142 and proximal end 144. Spool 140 includes a hollow central portion through the length of spool 140 to allow spool 140 to fit around main body 20 and slider 40. Spool 140 includes at least one, preferably two pins 146 that extend through slider channels 30 in main body 20 and are received within holes 48 in slider 40 to rigidly mount spool 140 with respect to slider 40, and constrain the freedom of movement of spool 140 and slider 40 with respect to main body.

Proximal end 144 of spool 140 includes a cutout section 148 that allows for spool 140 to slide over protruding portion 124 of button 120 when button 120 is compressed by the user against biasing spring 127. Further, cutout section 148 includes a shelf 148a that extends within recess 123 of button 120 between operable and protruding portions 122, 124 to retain slider 40 in the second position. Spool 140 additionally may include a plurality of ergonomic bumps or ridges 149 (FIG. 1) that are shaped to receive the fingers from a user's hand between bumps 149 to provide for an ergonomic grip of handle 10. Preferably, bumps 149 and thumb ring 25 on main body 20 are ergonomically formed to allow handle 10 to be held and manipulated by a single right or left hand of the user.

Figure 9:
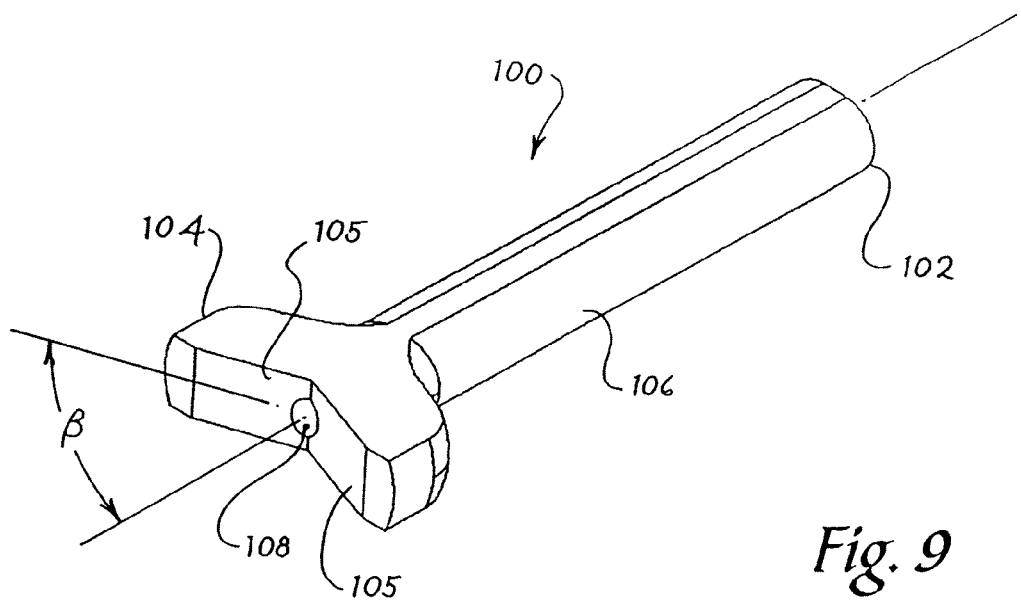
FIG. 9 is a perspective view of the rear gripper guide of the handle of FIG. 1.

Rear gripper guide 100 is best shown in FIG. 9 with reference to FIGS. 3a-3c. Rear gripper guide 100 includes a distal end 102, a proximal end 104, and a sliding core 106 that forms a majority of the length of rear gripper guide 100. Rear gripper guide 100 further includes a set of rear inclined faces 105. Rear inclined faces 105 are similar to front inclined faces 83 on front gripper guide 80, and are oriented at an oblique angle β with respect to longitudinal axis 36 of main body 20. Angle β may be any angle between about 45 degrees and about 89 degrees with respect to longitudinal axis 36 of main body. Preferably, angle β may be between about 60 degrees and about 80 degrees. More preferably, angle β may be about 70 degrees. In some embodiments, angle β may be complementary to angle α of grooves 32a, 32b.

Rear gripper guide 100 further includes an aperture 108 that extends through between distal and proximal ends 102, 104 of rear gripper guide 100 to provide space for the proximal end of the medical device to be threaded therethrough and engage rear grippers 70. A cannula 109 may be inserted through aperture 108 and extend through handle until reaching and being inserted through a portion of front gripper guide 80. Cannula 109 provides a smooth and consistent path for medical device to be threaded through handle to ensure that medical device easily travels past rear grippers 70 and through viewing window 26.

As discussed above, when slider 40 translates with respect to main body 20, springs 79 between main body 20 and rear grippers 70 become compressed and rear grippers 70 translate away from each other as rear grippers 70 slide along rear faces 105 of rear gripper guide 100 and projections 78 from rear grippers 70 slide within grooves 32a, 32b on main body 20. As slider 40 translates toward the first position, the biasing force from the springs 79 is decreased, allowing rear grippers 70 to slide along grooves 32a, 32b and rear faces 105 of rear gripper guide 100 until teeth 76 of rear grippers 70 contact the proximal end of the medical device.

In some embodiments, the components of handle 10 are sized such that spool 140 is translated approximately 10 mm between the first and intermediate positions. The handle is additionally preferably sized such that spool 140 is translated approximately 3 mm between the intermediate and second positions. Many representative medical devices that are usable with handle 10 required approximately 2-3 mm of stretch of the outer sheath with respect to the inner wire to cause the working portion of the medical device to translate to the biased position. The larger range of travel provided between the first and intermediate positions accounts for the variability of the actual required distance due to manufacturing tolerances and other parameters that have been observed during testing of representative medical devices.

Further, the required stretch of the outer sheath of a medical device may be more than the nominal 2-3 mm if the medical device is significantly coiled between the proximal end portion (that is being stretched by handle 10) and the working portion, which leads to less relative motion "felt" by the housing of the device (i.e. the portion holding and controlling the operation of the working portion) between the outer sheath and the inner wire for a given length of stretching. Additionally, the distance between the first, intermediate, and second positions could be other lengths when handle is used for different types of medical devices and other applications, depending on the amount of stretch required to operate the working portion of the medical device.

Figure 13A:
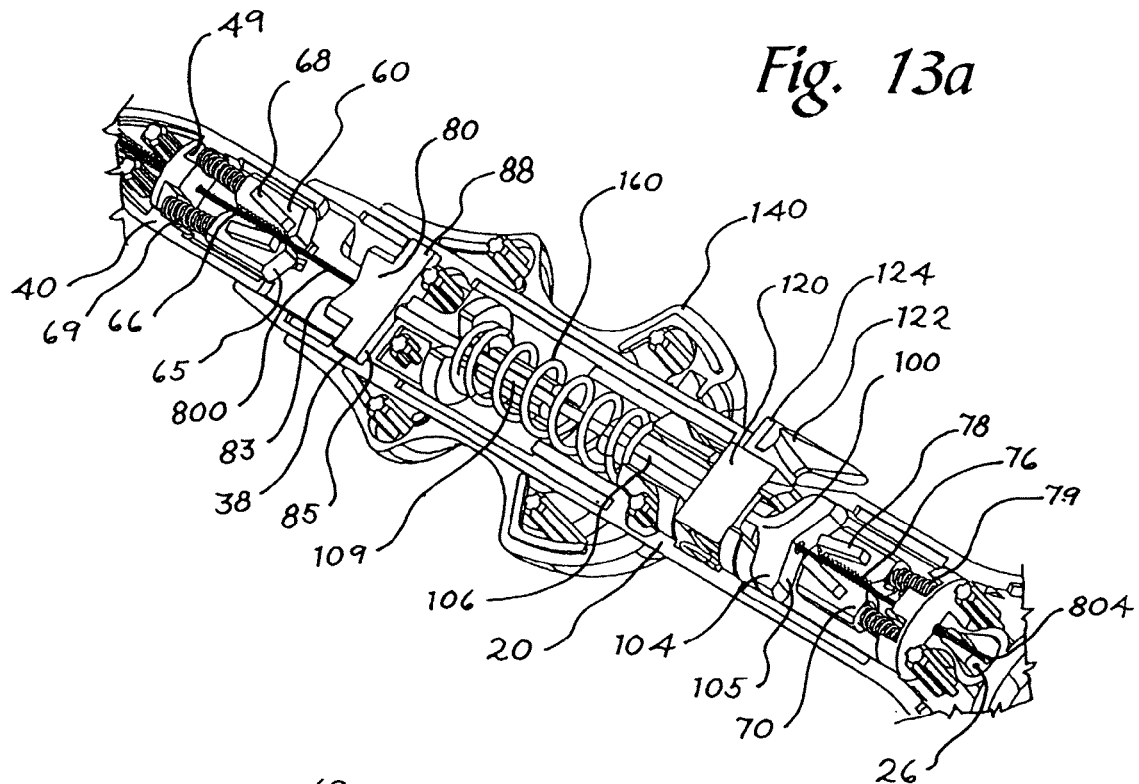
FIG. 13a is a perspective view of the view of FIG. 1a, with a portion of the main body, slider, and spool removed and the handle in the first position.

In operation, slider 40 is biased into the first position as shown in FIG. 3a with respect to main body 20 with main spring 160. When slider 40 is in the first position, both front and rear grippers 60, 70 are able to engage the medical device, as shown in FIG. 13a. To insert the medical device into handle 10, spool 140 may be pulled proximally toward button 120 with the users fingers. When pulling spool 140 proximally, the user depresses the operable portion 122 of button 120, which allows spool 140 to be pulled by the user fully rearward until slider 40 reaches the second position as shown in FIG. 3c, which allows spool 140 to be latched on retaining portion 124 of button 120. As slider 40 is pulled rearward with respect to main body 20, front and rear grippers 60, 70 selectively translate away from their respective opposing grippers 60, 70 due to the inclined faces 83, 105 of the respective front and rear gripper guides 80, 100 and the engagement between projections 68, 78 with corresponding grooves 46a, 46b and 32a, 32b.

Figure 13B:
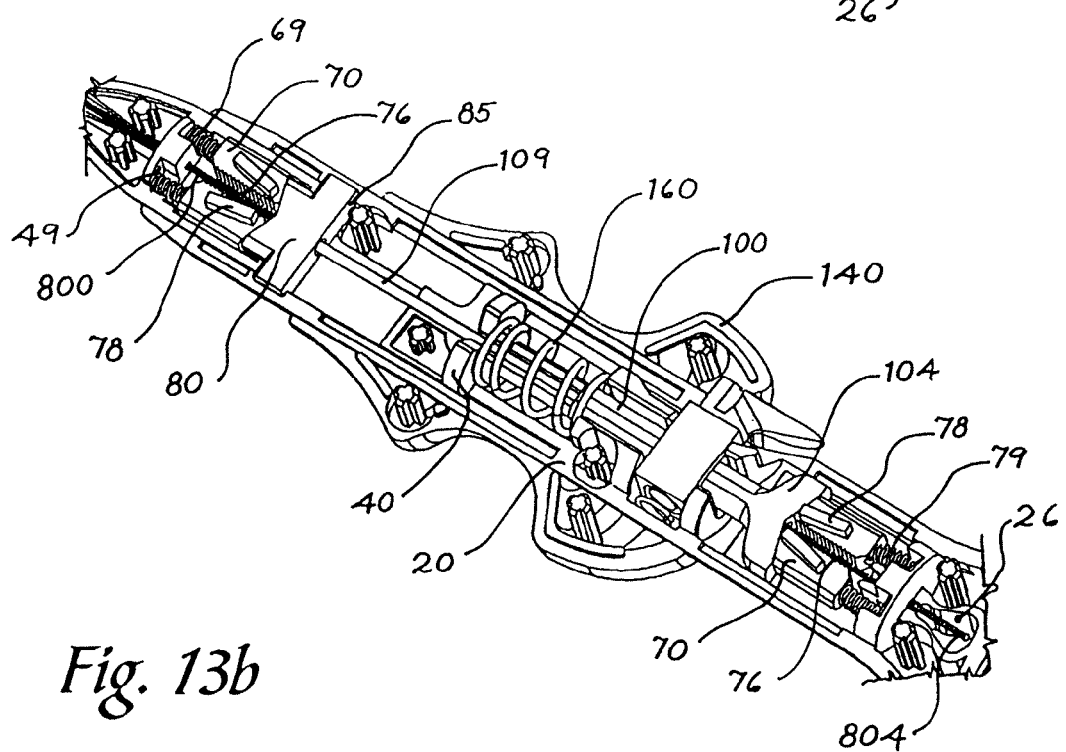
FIG. 13b is the view of FIG. 13a, showing the handle in the second position.

When slider 40 reaches the second position, button may be released and slider 40 is maintained in the second position due to the shelf 148a in spool 140 extending into recess 123 in button 120. Next, the proximal end portion of the medical device may be threaded through cavity 50 in slider 40 and through the remainder of handle 10 (through cannula 109 if provided) until the proximal end portion of the medical device can be seen through viewing window 26 in main body 20, as shown in FIG. 13b. As discussed above, because the working portion of the medical device may be significantly larger than the control portion, or proximal end of the medical device (and typically the lumen of the endoscope or similar medical device), the proximal end portion of the medical device must often be backwardly threaded through the length of the endoscope (or similar device) prior to being threaded through handle 10.

When the medical device is fully loaded into handle 10, button 120 is pressed and shelf 148a no longer engages recess 123. Slider 40 and spool 140 translate toward the first position due to the biasing force of main spring 160. As slider 40 translates with respect to main body 20, springs 69, 79 decompress and allow front and rear grippers 60, 70 to translate along grooves 32a, 32b and 46a, 46b such that the respective front and rear grippers 60, 70 travel toward the opposite front and rear grippers 60, 70.

As front and rear grippers 60, 70 travel toward each other, teeth 66, 76 for the respective front and rear grippers 60, 70 engage the outer sheath of the medical device. As slider 40 further slides toward the first position, front and rear grippers 60, 70 further slides toward the opposite respective gripper 60, 70, which maintains a strong hold wedge-like grip on the outer sheath. Components of handle 10 may be oriented and sized such that rear grippers 70 engage the medical device before the front grippers 60 engage the medical device. Generally, rear grippers 60 engage the medical device slightly before spool 140 passes the intermediate position (FIG. 3b) on the way to the first position and front grippers 60 engage the medical device slightly after spool 140 passes the intermediate position.

Figure 1A:
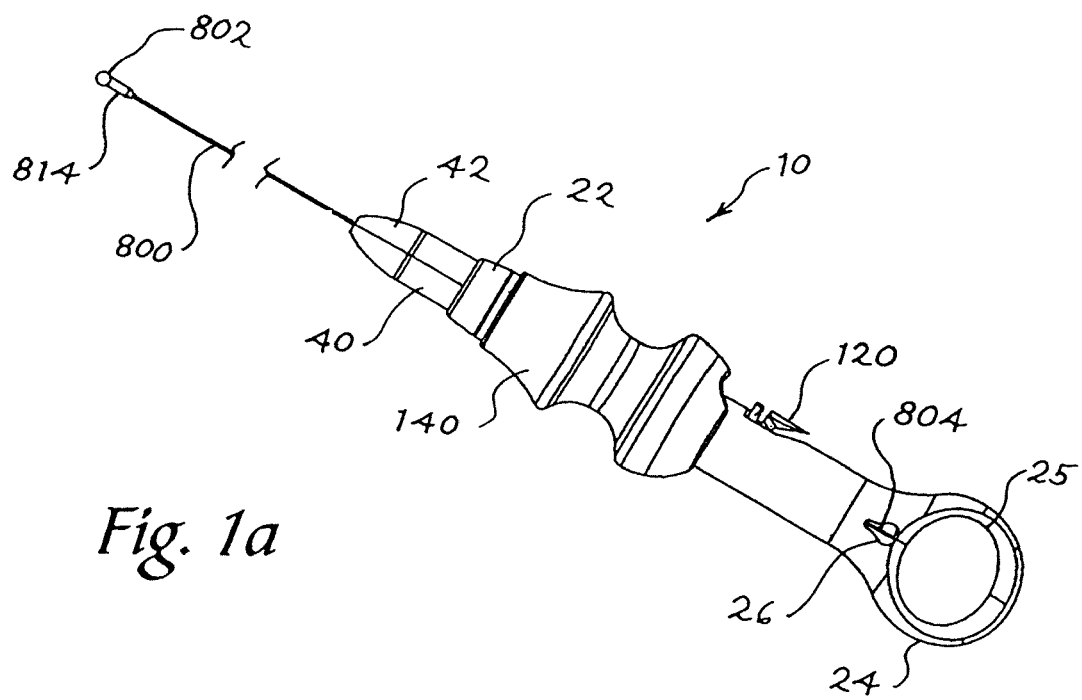
FIG. 1a is the handle of FIG. 1 in a first position with a medical device inserted therein.

Front and rear grippers 60, 70 slide in opposite directions away from each other, which places tension in the outer sheath of the proximal end portion of the medical device. When slider 40 reaches the first position (FIGS. 3a and 13a), the working portion of the medical device translated toward the biased position (i.e. where the biopsy cups 810 of the forceps device shown in FIG. 11 engage each other as shown in FIG. 1a) due to the tension in the outer sheath of the proximal end portion of the medical device, and the medical device is ready to be inserted into the patient with the endoscope, and through a urethral access sheath, if desired.

After the medical device and the endoscope are inserted into the patient, the working portion of the medical device may be transferred to the relaxed position. For example, in embodiments where handle 10 is used with a medical device with a set of pivotable biopsy cups, the medical device may have its biopsy cups opened to obtain a tissue sample, biopsy or for another purpose by manipulating handle 10 to pull spool 140 toward, but without pressing, button 120. As slider 40 translates with respect to main body 20, front and rear pairs of grippers 60, 70 selectively translate away from their respective opposite gripper at a predetermined position between the first position and the intermediate position. Preferably, only front grippers 60 disengage each other prior to spool 140 contacting protruding portion 124 of button 120, which removes the tension in the outer sheath of the proximal end of the medical device, but retains the contact between the rear grippers 70 and the proximal end portion of the medical device to prevent the medical device from being withdrawn from handle 10.

As front grippers 60 disengage the outer sheath of the medical device, the working portion of the medical device translates to the relaxed position. In embodiments where the medical device is a forceps device 800 similar to that shown in FIG. 11, the jaws 810 pivot away from each other to allow for a tissue sample or a biopsy. When spool 140 is released, spool 140 and slider 40 translate toward the first position due to the biasing force of main spring 160, and front grippers 60 reengage the outer sheath of the medical device, causing the working portion to rotate to the biased position as the front and rear grippers 60, 70 stretch the outer sheath of the proximal end portion of the medical device.

While the preferred embodiments of the disclosure have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A handle for remotely operating a medical device with a working portion and a control portion comprising:
   (a) a main body comprising a distal end, a proximal end, and a longitudinal axis between the distal and proximal ends;
   (b) a slider that is movable within the main body along the longitudinal axis; and
   (c) a first pair of grippers slidably connected to the slider and a second pair of grippers slidably connected to the main body and disposed proximally of the first pair of grippers, wherein the first pair of grippers is disposed within the slider and the second pair of grippers is disposed within the main body;
   wherein longitudinal movement of the slider with respect to the main body causes each of the first and second pairs of grippers to independently translate away from the longitudinal axis.

2. The handle of claim 1, wherein the control portion of the medical device is extendable between the first and second pairs of grippers.

3. The handle of claim 2, wherein the slider is movable with respect to the main body between a first position where the first and second pairs of grippers are engaged with the medical device, and a second position where the first and second pairs of grippers do not engage the medical device.

4. The handle of claim 3, further comprising a button that is translatable to selectively retain the slider in the second position with respect to the main body.

5. The handle of claim 4, wherein the button comprises a projecting portion provided to retain the slider in the second position.

6. The handle of claim 5, further comprising a spool that surrounds the main body and is substantially fixed to the slider, wherein the spool contacts the projecting portion of the button to prevent the slider from translating to the second position when the button is not compressed.

7. The handle of claim 6, wherein the first pair of grippers gripper do not engage the medical device when the spool contacts the projecting portion of the button with the button not compressed.

8. The handle of claim 2, further comprising a front gripper guide that is fixed to the main body, wherein the front gripper guide comprises a front end that engages a rear end of each of the first pair of grippers.

9. The handle of claim 8, wherein the front end of the front gripper guide comprises a face aligned at an oblique angle with respect to the longitudinal axis of the main body that are engageable with an angled rear end of each of the first pair of grippers.

10. The handle of claim 8, further comprising a rear gripper guide that is translatable within the main body with the movement of the slider, the rear gripper guide comprising a face aligned at an oblique angle with respect to the longitudinal axis of the main body that is engageable with an angled front end of each of the second pair of grippers.

11. The handle of claim 1, wherein the slider is biased distally along the main body by a main spring provided within the main body.

12. The handle of claim 3, wherein the working portion of the medical device is in a biased position when the slider is in the first position with respect to the main body and the control portion is received between the first and second pairs of grippers.

13. The handle of claim 1, wherein the first pair of grippers and the second pair of grippers each include a plurality of teeth, wherein each of the plurality of teeth are spaced from neighboring teeth by a length equal to a multiple number of diameters of an outer wire of the control portion of the medical device.

14. A handle for remotely operating a medical device with a working portion and a control portion comprising:
   (a) a main body comprising a distal end, a proximal end, and a longitudinal axis between the distal and proximal ends;
   (b) a slider that is movable within the main body along the longitudinal axis; and
   (c) a first gripper operatively connected to and disposed within the slider and a second gripper operatively connected to the slider and disposed proximally of the first gripper, wherein the second gripper is disposed within the main body;
   wherein longitudinal movement of the slider with respect to the main body causes the first and second grippers to change position, further comprising a front gripper guide that is fixed to the main body, wherein the front gripper guide comprises a front end that engages a rear end of the first grippers, and a first spring provided between a distal end of the slider and the first gripper to bias the first gripper toward the front gripper guide.

15. A handle for remotely operating a medical device with a working portion and a control portion comprising:
   (a) a main body comprising a distal end, a proximal end, and a longitudinal axis between the distal and proximal ends;
   (b) a slider that is movable within the main body along the longitudinal axis; and
   (c) a first gripper operatively connected to and disposed within the slider and a second gripper operatively connected to the slider and disposed proximally of the first gripper, and within second gripper is disposed within the main body;
   wherein longitudinal movement of the slider with respect to the main body causes the first and second grippers to change position, wherein the slider and the main body each comprise a groove to receive a corresponding projection that extends from the respective first and second grippers to define a range of travel of the first gripper with respect to the slider and the second gripper with respect to the main body.

16. The handle of claim 15, wherein the grooves on the slider and the main body are each defined at oblique angles with respect to the longitudinal axis of the main body.

17. A handle for remotely operating a medical device with a working portion and a control portion comprising:
   (a) a main body with a distal end, an opposite proximal end, and a longitudinal axis;
   (b) a slider disposed within the main body to translate between a first position and a second position with respect to the main body; and
   (c) a first pair of grippers disposed within the slider and a second pair of grippers disposed within the main body, wherein the first and second pairs of grippers selectively retain the control portion of the medical device therebetween by applying compressive contact upon the control portion when the slider is in the first position;

wherein the compressive contact upon the control portion is removed by the first and second pairs of grippers when the slider is in the second position such that the control portion of the medical device can be withdrawn from or inserted into the handle, wherein longitudinal movement of the slider from the first position toward the second position causes each gripper within each of the first and second pairs of grippers to independently translate away from the longitudinal axis.

18. The handle of claim 17, wherein the slider may be disposed in an intermediate position with respect to the main body between the first and second positions, wherein the second pair of grippers retains compressive contact upon the control portion of the medical device and the first pair of grippers releases the compressive contact upon the control portion of the medical device to allow the working portion to transfer to a relaxed position.

* * * * *

UNITED STATES PATENT AND TRADEMARK OFFICE
CERTIFICATE OF CORRECTION

| | | |
|---|---|---|
| PATENT NO. | : 8,016,856 B2 | Page 1 of 1 |
| APPLICATION NO. | : 11/945767 | |
| DATED | : September 13, 2011 | |
| INVENTOR(S) | : Shay Lavelle et al. | |

It is certified that error appears in the above-identified patent and that said Letters Patent is hereby corrected as shown below:

In column 13, claim 7, line 50, before "do not engage the medical" delete "gripper".

Signed and Sealed this
Twenty-ninth Day of November, 2011

David J. Kappos
*Director of the United States Patent and Trademark Office*